United States Patent [19]

McGregor

[11] 4,374,765

[45] Feb. 22, 1983

[54] MAMMALIAN COLLAGENASE INHIBITORS

[75] Inventor: William H. McGregor, Malvern, Pa.

[73] Assignee: American Home Products Corporation, New York, N.Y.

[21] Appl. No.: 309,368

[22] Filed: Oct. 7, 1981

[51] Int. Cl.³ .................... C07C 103/52; A61K 37/00
[52] U.S. Cl. ............................. 260/112.5 R; 424/177
[58] Field of Search .................. 424/117; 260/112.5 R

[56] References Cited

U.S. PATENT DOCUMENTS 4,235,885 11/1980 Sundoon et al. ..................... 424/177
4,276,284 6/1981 Brown ................................ 424/177

FOREIGN PATENT DOCUMENTS 53028165 8/1976 Japan ............................ 260/112.5 R

OTHER PUBLICATIONS

Ajinomoto, K. K., "Japanese Patent Abstract", 3028-165, 8-30-76.
Harper, "Ann. Rev. Biochem.", 1980, 49:1663-1078.

Primary Examiner—Delbert R. Phillips
Assistant Examiner—F. T. Meezie
Attorney, Agent, or Firm—Richard K. Jackson

[57] ABSTRACT

The polypeptides R-Gly-L-Cys-Gly-L-Glu-L-Glu-NH$_2$ or a pharmaceutically acceptable salt thereof act as collagenase inhibitors useful in the treatment of disease involving excessive tissue destruction by collagenase.

2 Claims, No Drawings

MAMMALIAN COLLAGENASE INHIBITORS

BACKGROUND OF THE INVENTION

Approximately thirty percent of the body protein of mammals is comprised of collagen, a long rod-like polypeptide containing three parallel chains of coiled-coil structure with a molecular weight of about 300,000. Collagen existing in skin, cartilage, bone and tendon is composed of two α1 chains and one α2 chain of roughly one thousand amino acids each. The α1 sequence is completely known and substantial sequences of the α2 chain have been elucidated.

Collagenase effects an ultra-specific cleavage of collagen at a site one quarter the length of the molecule from the C-terminus.

Collagenase is produced by rheumatoid synovial cells at a rate higher than it is produced by normal cells and the destructive events of rheumatoid arthritis can be correlated with the generation of collagenase. Collagenase has also been found to be involved in disease states resulting in tissue destruction of the stomach, eye, middle ear, peridontal membranes and skin. The administration of a collagenase inhibitor to prevent tissue destruction is an indicated method of treatment for disease states involving proteolytic destruction of collagen.

Collagenase is a metallo enzyme of molecular weight about 40,000 with a requirement of zinc. The enzyme is known to be inhibited by chelating agents such as ethylenediaminetetraacetic acid, o-phenanthroline, penicillamine and disulfide reducing agents such as cysteine and dithiothreitol as well as a number of poorly characterized naturally occurring substances.

DESCRIPTION OF THE INVENTION

In accordance with this invention there is provided a group of polypeptides which inhibit the activity of the enzyme collagenase. The polypeptides of this invention present the structural formula:

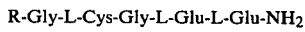

R-Gly-L-Cys-Gly-L-Glu-L-Glu-NH$_2$ in which
R is hydrogen, alkanoyl of 2 to 6 carbon atoms, cycloalkylcarbonyl of 6 to 8 carbon atoms or alkoxycarbonyl of 2 to 6 carbon atoms;
or a pharmaceutically acceptable salt thereof.

The pharmaceutically acceptable salts of the polypeptides of this invention include salts of the N-terminal amino group derived from either organic or inorganic acids such as acetic, lactic, succinic, benzoic, salicylic, methanesulfonic, toluenesulfonic, hydrochloric, sulfuric or phosphoric acid, and the like, as well as salts of glutamic acid such as the alkali metal, alkaline earth metal are mono- or di-alkylamine salts in which the alkyl groups contain from 1 to 4 carbon atoms. Desired salts may be produced from other salts via conventional treatment with ion exchange resins. The N-terminal acyl groups depicted as R in the structural formula, supra, are preferably alkanoyl or cycloalkanoyl moieties as defined and more preferably either the acetyl or cyclopentylcarbonyl groups.

The compounds of this invention are produced by conventional solution phase techniques or solid phase techniques employing a benzhydrylamine polystyrene resin support. Thus, the individual amino acids or preformed di- or tri-peptides necessary for the formation of the desired polypeptide or their activiated derivatives are condensed with formation of carbamide (—CONH—) bondings in the desired order of succession while temporarily protecting any reactive group which could undesirably enter into the condensation reaction. In the case of cysteine, the side chain mercapto protecting group may be acetamidomethyl, trityl, carbamoyl, thioethyl, thiotertiarybutyl or preferably p-methoxybenzyl. The applicable α-amino protecting groups are those well known to the art or preferably tert-butyloxycarbonyl. Similarly, any conventional protecting group may be employed with the α-carboxy group of glutamic acid although the benzyl group is preferred.

The inhibitory effect of the compounds of this invention toward collagenase was determined following the procedure of Sellers et al., Biochem. J. 167 353–360 (1977) whereby the 2mM of the inhibitor being tested is incubated at 35° C. for from 5 to 18 hours (depending upon the potency of the collagenase) with collagen and collagenase (buffered with Tris®—CaCl$_2$; pH 7.4). The collagen is acetyl $^{14}$C collagen. The samples are centrifuged and an aliquot removed for assay on a scintillation counter. Because native collagen forms insoluble fibrils under the test conditions, the supernatant liquid contains radioactivity as a measure of hydrolysis. The collagenase activity in the presence of 2mM inhibitor is compared to activity in a control devoid of hinibitor and the results reported as percent inhibition of collagenase activity. Each of the compounds of this invention have been established as active collagenase inhibitors by the test procedure.

Thus, the compounds of this invention are useful in the treatment of disease states involving excessive collagen destruction by collagenase such as rheumatoid arthritis and diseases evidenced by tissue destruction of the stomach, eye, middle ear, peridontal membranes, skin. The dosage of the collagenase inhibitors of this invention will vary with the mode of administration (oral, parenteral, topical, intramuscular, etc.) and the condition of the specific patient under treatment. Proper dosing may be readily established by initial administration of small amounts of the inhibitor, ca. 100 μg/kg. followed by increased doses until the optimum effect is achieved in a specific human or non-human mammalian patient. When sustained release treatment is desired, the polypeptides may be placed in conventional depot dosage forms such as a Silastic ® capsule or slow release pellet formulations conventional to the art.

The following example illustrates the preparation of a typical representative compound of the invention. The percent inhibition of collagenase activity at the 2mM concentration of polypeptide determined in accordance with the previously described standard testing procedure is provided after the preparative description.

EXAMPLE

CH$_3$CO-Gly-L-Cys-Gly-L-Glu-L-Glu-NH$_2$

10 Grams benzhydrylamine hydrochloride resin (Beckman) were treated twice in a solid phase peptide synthesizer with 30% triethylamine in MeCl$_2$ for five minutes and washed successively with MeCl$_2$, and DMF and coupled with 10 gm t-Boc γ-benzyl-L-glutamic acid, 4 gm. hydroxybenzotriazols (HOBT) diisopropylcarbodiimide (DIC) over the weekend in DMF. After washing with DMF (1 ×), MeCl$_2$ (2 ×), MeOH, and MeCl$_2$ the amino acyl resin was ninhydrin negative, was deprotected with 50% trifluoroacetic acid (TFA) in MeCl$_2$, washed with MeCl$_2$; 30% triethylamine in DMF (2 ×) and DMF (2 ×) and coupled with 10 g t-Boc γ-benzyl-L-glutamic, 4 gm HOBT and 4 ml DIC overnight in DMF. After washing as usual at this stage the peptidyl-resin was nonhydrin negative and was deprotected with TFA as previously described for this step, washed as described for this stage and coupled with 6 gm t-Boc glycine 4 gm HOBT and 4 ml DIC as usual. The peptidyl resin was ninhydrin negative after the usual washing at this stage was deprotected with TFA as previously described at this step, washed as usual and coupled with 10 gm t-Boc-S-p-methoxybenzyl-L-cysteine, 4 gm HOBT and 4 ml DIC as usual. After the usual washing the peptidyl resin was ninhydrin trace positive and was recoupled with 5 gm t-Boc-S-p-methoxybenzyl-L-cysteine 2 gm HOBT and 2 ml DIC in the previously described manner for this step. After the usual washing the peptidyl resin was still ninhydrin trace positive and was deprotected as usual with TFA washed as previously described and coupled with 6 gm t-Boc glycine, 4 gm HOBT and 4 ml DIC in the usual manner. The peptidyl resin was ninhydrin negative after the usual washing at this stage, was deprotected with TFA, washed as usual, and coupled with 5 gm acetyl imidazole in MeCl$_2$ overnight and after washing was again coupled with 5 gm acetyl imidazole in MeCl$_2$ overnight. Washed as usual at this stage and with Et$_2$O and dried in vacuo.

The above peptidyl resin was deprotected and cleaved with HF in the presence of 10 ml of anisole for 1 hour at 0° C. The HF was removed in vacuo the residue washed 3 times with Et$_2$O dried in a stream of N$_2$, triturated with 150 ml of 0.2 N HOAc and lyophylized to give 1.5 gm crude peptide.

The crude product (150 ml) was purified on Sephadex G-10 using 0.2 N HOAc at flow rate of 15 ml/hr and collecting 1 ml fractions. Fractions 58–64 were combined on the basis of TLC (S.G. BAW peptide chlorine spray) and lyophylized 44 mg. Amino Acid Ratio: Gly 1.0, Glu 1.02. Cys recovered but not quantitated. Percent collagenase inhibition: 80.

What is claimed is:
1. A compound of the formula:

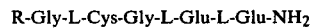

R-Gly-L-Cys-Gly-L-Glu-L-Glu-NH$_2$ in which

R is hydrogen, alkanoyl of 2 to 6 carbon atoms, cycloalkylcarbonyl of 6 to 8 carbon atoms or alkoxycarbonyl of 2 to 6 carbon atoms;

or a pharmaceutically acceptable salt thereof.

2. The compound of claim 1 which is CH$_3$CO-Gly-L-Cys-Gly-L-Glu-L-Glu-NH$_2$ or a pharmaceutically acceptable salt thereof.

* * * * *